United States Patent [19]

Grantham

[11] 4,287,753

[45] Sep. 8, 1981

[54] AUTOMATIC MOISTURE CONTROLLER WITH STACK SENSOR

[76] Inventor: Frederick W. Grantham, 12055 Goshen Ave., Los Angeles, Calif. 90049

[21] Appl. No.: 172,083

[22] Filed: Jul. 24, 1980

[51] Int. Cl.³ .................. G01N 27/04; F26B 21/08
[52] U.S. Cl. .......................................... 73/29; 34/89
[58] Field of Search .............. 73/29, 336.5; 340/602; 338/35; 324/65 R; 236/44 R, 44 A, 44 E; 34/50, 54, 89

[56] References Cited

U.S. PATENT DOCUMENTS

| | | | |
|---|---|---|---|
| 2,407,215 | 9/1946 | Anderson | 15/250.02 |
| 2,715,667 | 8/1955 | Auwarter | 338/35 |
| 2,733,607 | 2/1956 | Miller | 73/29 |
| 2,819,614 | 1/1958 | Sion | 73/29 |
| 2,904,765 | 9/1959 | Seehof et al. | 73/336.5 |
| 2,930,016 | 3/1960 | Weston et al. | 338/35 |
| 3,350,941 | 11/1967 | Misevich et al. | 73/336.5 |
| 3,424,977 | 1/1969 | Krobath | 340/602 |
| 3,436,838 | 4/1969 | Helfrich | 34/45 |
| 3,467,860 | 9/1969 | Trischberger | 324/61 R |
| 3,521,376 | 7/1970 | Beller | 34/45 |
| 3,555,289 | 1/1971 | Sobkow | 307/10 R |
| 4,207,562 | 6/1980 | Kaylor et al. | 340/602 |
| 4,221,058 | 9/1980 | Zagorzycki | 73/29 |

Primary Examiner—Stephen A. Kreitman
Attorney, Agent, or Firm—Henry M. Bissell

[57] ABSTRACT

A moisture detector and controller including a pair of spaced-apart plates positioned in a moist air duct, a cleaner positioned between the plate surfaces adapted to wipe them upon initiation and termination of air flow, and an associated circuit effective to measure the resistance between the plates and compare it with a preselected reference resistance indicative of a desired humidity of the air present in the duct.

13 Claims, 5 Drawing Figures

AUTOMATIC MOISTURE CONTROLLER WITH STACK SENSOR

BACKGROUND OF THE INVENTION

1. Field of the Invention

The present invention relates to humidity control and especially to sensing the amount of moisture contained in heated exhaust air in laundry dryers to permit control of the dryer.

2. Description of the Prior Art

Generally, it has been recognized that it is desirable to sense the moisture content of clothes or other laundry articles during drying operations. Clothes may be taken out of the dryer prior to the moisture level being sufficiently low for them to be dry or they may be left in a dryer too long, resulting in excess drying, which causes scorching and is wasteful of energy. Thus, the prior art has suggested methods of detecting the moisture remaining in the articles being dried. Conventionally, these are placed within the drying chamber and the articles are tumbled about in close proximity to the sensors. This type of system, however, presents a significant problem in that the surfaces of the humidity sensor quickly become corroded and fouled with lint and other material. Thus, they must be cleaned frequently and are apt to provide false readings. Helfrich in U.S. Pat. No. 3,436,838 and Beller in U.S. Pat. No. 3,521,376 disclose exemplary clothes drying systems.

Numerous other systems have also been suggested in the art that utilize moisture sensors. For example, Anderson U.S. Pat. No. 2,407,215 and Sobkow U.S. Pat. No. 3,555,289 both disclose automobile windshield wiper systems actuated by moisture deposited between electrodes located in the wiper path. In another system, Trischberger U.S. Pat. No. 3,467,860 discloses a method of testing the moisture content in a solid.

Numerous other systems and electrode configurations for humidity sensors are disclosed in the art. For instance, see Auwarter U.S. Pat. No. 2,715,667, Miller U.S. Pat. No. 2,733,607, Seehof et al U.S. Pat. No. 2,904,765 and Weston et al U.S. Pat. No. 2,930,016. In each of these cases, the electrodes of the sensors are narrowly separated by a solid humidity-sensitive conductor. Also, it has been suggested that humidity changes be determined by sensing capacitance changes utilizing a narrow insulated gap between two electrodes. This type of system is embodied in Misevich et al U.S. Pat. No. 3,350,941 and Krobath U.S. Pat. No. 3,424,977. Lastly, the use of widely spaced electrodes has been suggested in Sion U.S. Pat. No. 2,819,614 to measure resistivity changes in a thermistor heated by current flow to an adjoining electrode.

Thus, it is clear that there is a need in the art for a moisture detecting system which is simple and low cost and still be accurate in its operation. The need is also apparent for a system that will not interfere with the drying of clothing or laundered materials, and which will accurately indicate when the articles are sufficiently dry. It is to these ends that the present invention is directed.

SUMMARY OF THE INVENTION

The present invention is directly related to the production of a system which is relatively maintenance free and can be utilized in numerous size drying operations to sense the moisture content of the articles being dried while not interfering with the drying operation itself. In the apparatus, either a circulation or a exhaust duct for the dryer it utilized. Depending on which duct is utilized, different resistivities and calibrations are employed since these could have an effect on the operation of the system, even though proper calibration will alleviate any significant problems.

In one form of the present invention, a pair of conductive plates are mounted inside the selected duct in a manner such that they do not significantly restrict the flow of air through the duct. This is accomplished, for example, by a pair of braced brackets insulated from the sidewalls of the duct and positioned adjacent the sidewalls. The two plates are spaced a fixed distance apart and have a flap-type structure mounted between them. The pivotable flap is supported off-center so as to form a counterweight and is provided with abrasive edges which ride against the surfaces of the plates with sufficient contact force to clean and wipe the plates and yet be relatively free moving during operation. The plates are preferably vertically oriented in the duct so that when the blower or other air circulating apparatus is off, the flap riding between the plates will rest in a lowered position partially blocking the duct. When the blower is turned on and air circulated within the system, the air pressure will move the flap across the conductive surfaces, wiping them clean, and will be pivoted to a raised position which is not restrictive of air flow through the duct and which does not affect the true resistance reading of the air between the plates. Each of the plates is connected by a separate lead to, for instance, a Wheatstone bridge, which can be used to measure the resistance across the plates. The bridge is calibrated to make the appropriate measurements of resistance between the plates, and is adjustable so that the operator can select a degree of dryness corresponding to a preselected duct air humidity. Once the resistance between the two plates reaches this preselected level, then the bridge provides an output signal which may take the form of a light, a buzzer, an automatic shut-off for the dryer or a desired combination thereof.

Optionally, a wall portion of the duct, if appropriately insulated, may be utilized as one of the plates when a rectangular or square duct is utilized. In this manner, a further improvement of the air flow in the internal structure in the duct is provided which, for instance, further minimizes the increase in the resistance to air flow across the system. Of course, when utilizing this single plate form, it is important to insure that the duct portion is sufficiently insulated from the remainder of the system and that the spacing characteristics utilized for the unit, which are based on the design characteristics of the ducting, are appropriately maintained in order to avoid erroneous readings. Numerous variations of the present invention may be utilized for the resistance measurements. For instance, a cylindrical electrode could be positioned within and insulated from a cylindrical duct, so long as both are maintained coaxially positioned.

Each of the two plates is provided with an electrical lead and the leads are connected to, e.g., the Wheatstone bridge as noted above. The measurement of the resistance across the gap betweeen the two plates depends upon the humidity of the air passing between the plates. As a result, the system can be calibrated such that when a preselected humidity is obtained, the Wheatstone bridge is balanced. The balancing of the Wheatstone bridge can be utilized to signal the operator through a light or buzzer that the drying cycle is completed, or the balancing signal from the Wheatstone bridge may be utilized to automatically shut off the dryer or to cycle the burner on and off, as desired.

BRIEF DESCRIPTION OF THE DRAWINGS

A better understanding of the present invention may be had from the following detailed description, taken in conjunction with the drawings in which.

DESCRIPTION OF THE PREFERRED EMBODIMENTS

Figure 1:
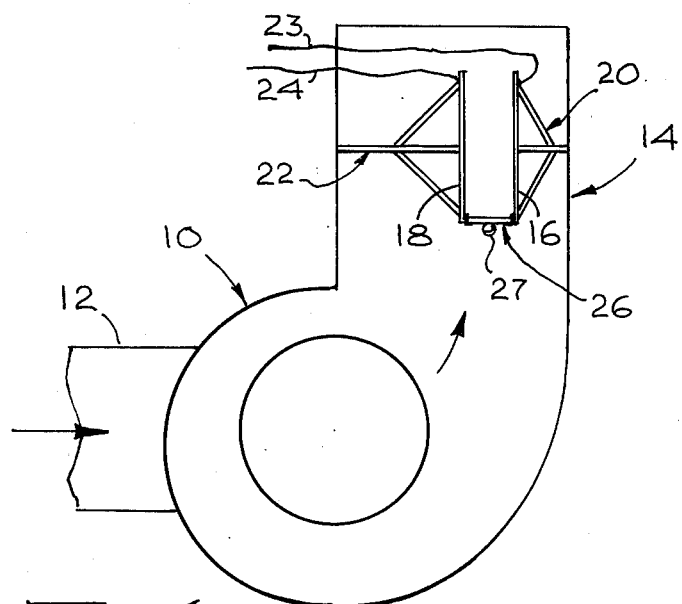
FIG. 1 is a schematic side view of the apparatus of the present invention.

The present invention will be described in terms of a commercial laundry dryer. However, it is to be understood that the invention is applicable to other drying operations, such as those situations where a multiplicity of individual items are being dried in a particular container or on a continuous basis through the use of heated or heated and dried inlet air being passed over and around the articles. In this light, in FIG. 1, blower 10 draws air from duct 12 in the direction indicated by the arrow and causes it to circulate out and upward through duct 14. The air passes between conductive plate electrodes 16 and 18 which are held in position by mounting brackets 20 and 22 respectively. Mounting brackets 20 and 22 are specifically designed so that they provide minimal resistance to the air flow through duct 14. Also, in order to insure accurate readings, electrodes 16 and 18 are insulated from the external portion of duct 14 by appropriate insulation, either at the points of contact of the mounting brackets and the electrodes or at the points of contact between the mounting brackets and the walls of the duct (or both). Each electrode is provided with a lead 23 or 24 which is connected to associated circuitry such as a Wheatstone bridge, as is described further in FIG. 2. A pivotable flap or other cleaning member 26 is mounted along the bottom area of the two electrodes and retained in its horizontal position by stop 27. The flap is pushed upward by the air pressure from blower 10 and contacts the internal surfaces of the two electrodes during rotation about its pivot axis in order to clean the surfaces of the electrodes, as can be better seen FIG. 3.

Figure 2:
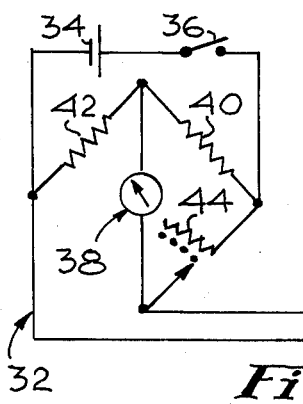
FIG. 2 is a top view of the apparatus of FIG. 1.

In FIG. 2, the electrodes 16 and 18 are shown connected with mounting brackets 20 and 22 to the walls of duct 14. Mounting brackets 28 are also shown connected to hinges 30 which pivotably support flap 26 for rotation upon impingement of air pressure. Stop 27 is also shown in appropriate position. Leads 23 and 24 are shown in FIG. 2 as connected to Wheatstone bridge 32 which is provided with resistances 40, 42 and variable resistor 44. The bridge is supplied with power through battery 34 and activated by switch 36. When turned on, and an appropriate resistance selected through variable resistor 44, the resistance between electrodes 16 and 18 reaches the level predetermined in the system, the current indicated by signal generator 38 will be zero and the selected indicia of humidity will be obtained, since the resistance between the two plates decreases with increases in humidity. This zero reading can be used by an operator to shut off the heating and blowing steps for the dryer, or in the alternative, a zero reading can be utilized to set off a buzzer or a light, or automatically turn off the dryer, or other means, as are conventionally known in the art.

Figure 3:
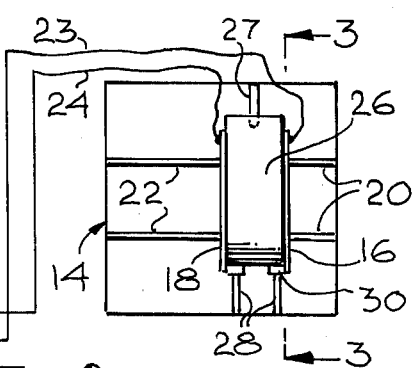
FIG. 3 is a section taken along lines 3—3 of FIG. 2.
Figure 3:
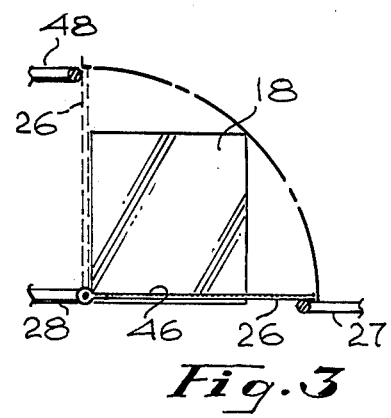

In FIG. 3, a sectional view taken along lines 3—3 of FIG. 2, plate 18 is depicted from its side. Associated flap 26 is resting on stop 27 and hinged to brackets 28. Support flap 26 has abrasive member 46 which is exposed in this view, taken just inside of plate 16 of FIG. 2. An equivalent abrasive member is also provided on the opposite edge of flap 26, adjacent plate 18. These abrasive members 46 may be thin wire brushes which are effective to remove build-up from the faces of the plates 16, 18 with each pass of the wiper or flap 26. As shown, secondary stop 48 is used to hold flap 26, shown here in phantom, in substantially vertical position during operation of the dryer.

Figure 4:
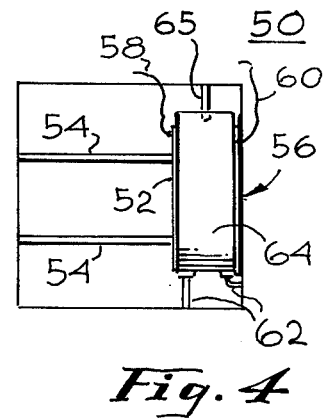
FIG. 4 shows an alternative embodiment of the invention.

In the optional embodiment shown in FIG. 4, duct 50 has plate 52 mounted via brackets 54 on one side of it. The second plate is provided by insulating a section of opposite wall 56 from the remainder of the opposite wall and thus providing a separate integral plate along wall 56. Thus plates 52 and 56 are provided with leads 58 and 60, respectively, which are connected to the Wheatstone bridge or other signal comparing and generating circuit as discussed hereinabove. In this embodiment, mounting brackets 62 are supplied to position flap 64 in conjunction with stop 65 in the same manner as the other embodiments of the present invention.

Figure 5:
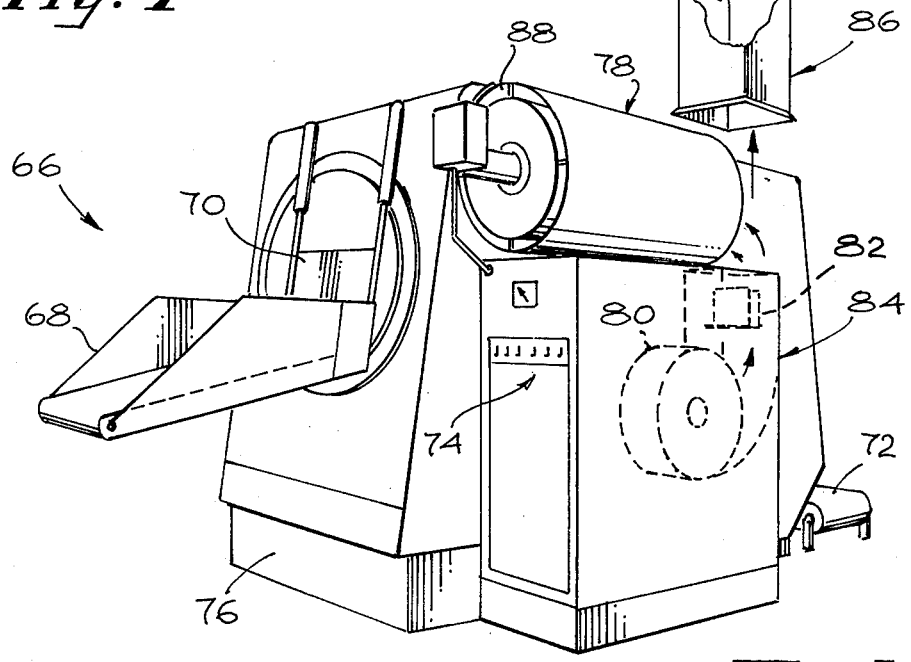
FIG. 5 shows a commercial type laundry dryer incorporating the apparatus of the invention.

In FIG. 5, a commercial dryer indicated as 66 is provided with supply means 68, inlet door 70 and finished article conveyor 72. The dryer is mounted on support structure 76 along with control unit 74 and burner 78. Air from inside of dryer 66 is drawn outwardly by blower 80 and blown past sensors 82, which are mounted in duct 84 in the same manner as that shown in FIG. 1. The sensors are connected by circuitry, not shown, to the front panel control system 74. In this manner, the air exiting the dryer in its humidified state is passed over the plates of sensor 82, and the humidity of the air in the dryer is determined. A portion of this heated air passes into burner 78, as indicated by the arrows, and the remainder of it is exhausted through duct 86. The portion travelling into burner 78 is heated along with intake air, at least partially drawn in through fins 88 as well as through the open area between ducts 84 and 86. In this manner partial recirculation of the heated air along with the injection of fresh air for heating is provided to maximize the efficiency of the unit. In addition, sensor 82 could be located at other positions, for instance in exhaust duct 86 as shown in phantom outline, designated 82'.

Although there have been described above specific arrangements of a humidity sensor for a commercial dryer in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined by the appended claims.

What is claimed is:

1. Moisture detecting apparatus comprising:
    a duct for the passage of moist air;
    a pair of opposed spaced-apart conductive plates mounted in said duct;

a wiper adapted to selectively traverse the facing surfaces of said plates; and sensing means connected to said plates effective to measure the resistance between the plates and provide an indication of relative humidity of the air between the plates.

2. The apparatus of claim 1 wherein the sensing means comprises a Wheatstone bridge.

3. The apparatus of claim 2 further including means for generating a signal when the resistance between the plates reaches a predetermined level corresponding to a preselected humidity.

4. The apparatus of claim 1 wherein the wiper comprises a pivotable flap positioned between the plates.

5. The apparatus of claim 4 wherein the flap is adapted to be moved across the faces of the plates by the flow of gases in the duct.

6. The apparatus of claim 1 wherein one opposed surface is formed by an insulated section of said duct.

7. The apparatus of claim 1 wherein the plates are mounted in a vertical section of the gas exhaust duct of a commercial dryer immediately downstream from the blower.

8. The apparatus of claim 1 wherein the plates are mounted in the stack duct for exhausting gases from a commercial dryer.

9. The apparatus of claim 1 wherein the wiper further comprises cleaning means for wiping across the facing surfaces of the plates.

10. The apparatus of claim 9 wherein the cleaning means further comprises abrasive portions extending from edges of the wiper to contact the facing surfaces of the plates.

11. The apparatus of claim 10 wherein the abrasive portions comprise wire brushes.

12. The apparatus of claim 5 wherein the flap is pivotably mounted in an off-center position to develop a counterbalance force effective to restore the flap to a horizontal position upon cessation of gas flow in the duct.

13. The apparatus of claim 5 wherein the flap is mounted to be pivoted out of position between the faces of the plates when moved by the gas flow in the duct in order to avoid affecting the resistance measurement between the plates.

* * * * *